(12) United States Patent
Ahluwalia et al.

(10) Patent No.: US 6,414,017 B2
(45) Date of Patent: *Jul. 2, 2002

(54) INHIBITION OF HAIR GROWTH

(75) Inventors: Gurpreet S. Ahluwalia, Potomac; Douglas Shander, Gaithersburg, both of MD (US)

(73) Assignee: The Gillette Company, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/765,106

(22) Filed: Jan. 18, 2001

Related U.S. Application Data

(63) Continuation of application No. 09/584,281, filed on May 31, 2000, now abandoned, which is a continuation-in-part of application No. 08/068,257, filed on May 28, 1993, now Pat. No. 6,248,751, and a continuation-in-part of application No. 08/068,256, filed on May 28, 1993, now Pat. No. 6,239,170.

(51) Int. Cl.⁷ .................... A61K 31/355; A61K 31/235; A61K 31/05; A61K 31/19
(52) U.S. Cl. ................. 514/458; 514/544; 514/570; 514/734; 514/880
(58) Field of Search ................. 514/880, 458, 514/544, 570, 734

(56) References Cited

U.S. PATENT DOCUMENTS

| | | |
|---|---|---|
| 3,426,137 A | 2/1969 | Philpitt |
| 4,039,669 A | 8/1977 | Beyler et al. |
| 4,139,638 A | 2/1979 | Neri et al. |
| 4,161,540 A | 7/1979 | Neri et al. |
| 4,191,775 A | 3/1980 | Glen |
| 4,269,831 A | 5/1981 | Ferrari et al. |
| 4,344,941 A | 8/1982 | Weichert et al. |
| 4,370,315 A | 1/1983 | Greff et al. |
| 4,439,432 A | 3/1984 | Peat |
| 4,530,844 A | 7/1985 | Smerbeck et al. |
| 4,720,489 A | 1/1988 | Shander |
| 4,877,789 A | 10/1989 | Shroot |
| 4,885,289 A | 12/1989 | Breuer et al. |
| 5,095,007 A | 3/1992 | Ahluwalia |
| 5,096,911 A | 3/1992 | Ahluwalia et al. |
| 5,132,293 A | 7/1992 | Shander et al. |
| 5,143,925 A | 9/1992 | Shander et al. |
| 5,189,212 A | 2/1993 | Ruenitz |
| 5,271,942 A | 12/1993 | Heverhagen |
| 5,300,284 A | 4/1994 | Wiechers et al. |
| 5,364,885 A | 11/1994 | Ahluwalia et al. |
| 5,411,991 A | 5/1995 | Shander et al. |
| 5,928,654 A | 7/1999 | Duranton |

FOREIGN PATENT DOCUMENTS

| | | |
|---|---|---|
| EP | 0 413 528 A1 | 2/1991 |
| EP | 0 532 219 A2 | 3/1993 |
| EP | 0 648 488 A1 | 4/1995 |
| GB | 1 458 349 | 12/1976 |
| GB | 1458349 | 12/1976 |
| JP | 02017115 | 7/1988 |
| JP | 1-96126 | 4/1989 |

OTHER PUBLICATIONS

Laughton et al., Inhibition of Mammalian 5–Lipoxygenase and Cyclo–Oxygenase by Flavonoids and Phenolic Dietary Additives, Biochemical Pharmacology, vol. 42, No. 9, pp. 1673–1681, 1991.
Day et al., Clinical Pharmacology of Non–Steroidal Anti–Inflammatory Drugs, Pharmac. Ther. vol. 33, pp. 383–433, 1987.
Database WPI, Week 8441, Derwent Publications Ltd., London, GB, AN 84–254475 and JP A 59 155 314 (Rikagaku Kenkyusho) (Sep. 1984) Abstract.
S.T.N. File Supplier, Karlsruhe, DE, File Chemical Abstracts, vol. 101, n. 2087 (1984).
Goos et al., Arch. Dermatol. Res. (1982) 273:333–341.
Girard et al., Arch. Dermatol. Res. (1980) 269:281–290.
Simpson et al., British Journal of Dermatology (1979) 100, 687.
Sato, The Hair Cycle and its Contol Mechanism, Biology and Disease of the Hair, 3–13 (1975).
Burdick et al., British Journal of Dermatology (1970) 82, Supplement 6, 10.
Champion, Therapeutic Usage of the Non–Steroidal Anti–Inflammatory Drugs, The Medical Journal of Australia, vol. 149, Aug. 15, 1968.
Higgs et al., The Mode of Action of Anti–Inflammatory Drugs Which Prevent the Peroxidation of Arachidonic Acid, Anti–rheumatic Drugs, pp. 11–36, 1983.

*Primary Examiner*—Alan Siegel
(74) *Attorney, Agent, or Firm*—Fish & Richardson P.C.

(57) ABSTRACT

Mammalian hair growth is reduced by applying to the skin a composition including an inhibitor of an enzyme involved in arachidonic acid metabolism.

21 Claims, No Drawings

INHIBITION OF HAIR GROWTH

This is a continuation of U.S. application Ser. No. 09/584,281, filed May 31, 2000, abandoned, which is a continuation-in-part of U.S. application Ser. No. 08/068,257, filed May 28, 1993, now U.S. Pat. No. 6,248,751, issued Jun. 19, 2001, and U.S. application Ser. No. 08/068,256, also filed May 28, 1993, now U.S. Pat. No. 6,239,170.

The invention relates to the inhibition of hair growth.

Arachidonic acid is released from membrane lipids in response to injury or other irritation. The enzyme cyclooxygenase converts arachidonic acid into cyclic endoperoxides commonly known as $PGG_2$ and $PGH_2$. The endoperoxides subsequently are converted into prostoglandins, which are the primary mediators of inflammation in the body.

The enzyme 5-lipoxygenase converts arachidonic acid into 5-hydroperoxyercosa-6,8,11,14-tetraenoic acid, which subsequently is converted into a family of compounds known as leukotrienes. The exact biological role of leukotrienes has not yet been determined.

It has now been found that mammalian (including human) hair growth can be inhibited by applying to the skin a composition including an inhibitor of an enzyme involved in arachidonic acid metabolism in an amount effective to reduce hair growth in the applied area. The inhibitor may, for example, be an inhibitor of cyclooxygenase or lipoxygenase, or may inhibit both enzymes.

Some preferred inhibitors are commonly known as non-steroidal anti-inflammatory drugs (NSAIDs). These drugs include compounds from a variety of chemical classes.

One preferred class of NSAIDs are propionic acids, which include α-methyl-4-[2-methylpropyl]benzeneacetic acid (ibuprofen), 6-methoxy-α-methyl-2-naphthaleneacetic acid (naproxen), 2-[3-phenoxyphenyl]propionic acid (fenoprofen), 2-[3-benzoylphenyl]propionic acid (ketoprofen), gamma-oxo-[1,1'-biphenyl]-4-butanoic acid (fenoprofen), and 6-chloro-α-methylcarbazole-2-acetic acid (carprofen).

Another preferred class of NSAIDs are indoleacetic acids, which include 1-[p-chlorobenzoyl]-5-methoxy-2-methylindole-3-acetic acid (indomethacin), 5-fluoro-2-methyl-1-[(4-(methylsulfinyl)phenyl) methylene]-1H-indene-3-acetic acid (sulindac), 1-methyl-5-[p-toluoyl] pyrrole-2-acetic acid (tolmetin), 2-[(2,6-dichlorophenyl) amino]-benzeneacetic acid (diclofenac).

A third preferred class of NSAIDs are salicylates, which include 2-acetoxybenzoic acid (acetylsalicylic acid) and 5-[2,4-difluorophenyl]salicylic acid (diflunisal).

A fourth preferred class of NSAIDs are anthranilic acids, which include 2-[(2,6-dichloro-3-methylphenyl) amino] benzoic acid (meclofenamic acid) and 2-[(2,3-dimethylphenyl) amino]benzoic acid (mefenamic acid).

A fifth preferred class of NSAIDs are enolic acids, such as 4-hydroxy-2-methyl-N-2-pyridinyl-2H-thieno[2,3-e]-1,2-thiazine-3-carboxamide-1,1-dioxide (tenoxicam).

Other NSAIDs like 4-[6-methoxy-2-naphthyl]-2-butanone (nabumetone) also can be used.

Examples of other inhibitors that have been found effective in reducing hair growth include quercetin (3,3',4',5,7-pentahydroxy flavone), dl-α-tocopherol, apigenin (4',5,7-trihydroxy flavone), propyl gallate, NDGA (nordihydroguaiaretic acid), and caffeic acid (3,4-dihydroxycinnamic acid). All of these compounds are known in the art and are commercially available. Other inhibitors are known in the art; see, for example, Laughton et al., 42 Biochemical Pharmacology 1673 (1991).

The composition preferably includes a non-toxic dermatologically acceptable vehicle or carrier which is adapted to be spread on the skin. Examples of suitable vehicles are acetone, alcohols, or a cream, lotion, or gel which can effectively deliver the active compound. In addition, a penetration enhancer may be added to the vehicle to further enhance the effectiveness of the formulation.

The concentration of the inhibitor in the composition may be varied over a wide range up to a saturated solution, preferably from 1 to 30% by weight or even more; the reduction of hair growth increases as the amount of inhibitor applied increases per unit area of skin. The maximum amount effectively applied is limited only by the rate at which the inhibitor penetrates the skin. Generally, the effective amounts range from 100 to 3000 micrograms or more per square centimeter of skin.

The composition should be applied to the area of the body where it is desired to inhibit hair growth. Typically, the composition can be applied to the face, particularly to the beard area of the face, i.e., the cheek, neck, upper lip, and chin. The composition can also be applied to the legs, arms, torso or armpit. The composition is particularly suitable for the treatment of hirsutism. In humans, the composition should be applied once or twice a day, or even more frequently, for at least three months to achieve a perceived reduction in hair growth.

Reduction of hair growth is demonstrated when the frequency of hair removal is reduced, or the subject perceives less hair on the treated site, or quantitatively, when the weight of hair removed by shaving (i.e., hair mass) is reduced. Male intact Golden Syrian hamsters are considered acceptable models for human beard hair growth in that they display oval shaped flank organs, one on each side, each about 8 mm. in major diameter, which grow thick black and coarse hair similar to human beard hair. These organs produce hair in response to androgens in the hamster.

To evaluate the effectiveness of a particular inhibitor in reducing hair growth, the flank organs of each of a group of hamsters are depilated by applying a thioglycolate based chemical depilatory (Surgex). To one organ of each animal 10 μl. of vehicle alone once a day is applied, while to the other organ of each animal an equal amount of vehicle containing the inhibitor is applied. After thirteen applications (one application per day for five days a week), the flank organs are shaved and the amount of recovered hair (hair mass) from each is weighed. Percent-reduction of hair growth is calculated by subtracting the hair mass (mg) value of the test compound treated side from the hair mass value of the vehicle treated side; the delta value obtained is then divided by the hair mass value of the vehicle treated side, and the resultant number is multiplied by 100.

Some preferred inhibitors were tested according to the above procedure. The results are presented in Table 1; the vehicles used to deliver the inhibitors are reported in Table 2.

TABLE 1

| | | | | Hair Mass | | |
|---|---|---|---|---|---|---|
| Compound | Dose | Vehicle | pH | Treated (mg) | Control (mg) | Percent Inhibition |
| Propionic acids | | | | | | |
| Ibuprofen | 20% | B | 5.0 | 1.160 ± .16 | 1.704 ± .15 | 30.33 ± 7.74 |
| Naproxen | 20% | A | 8.5 | 0.771 ± .11 | 2.108 ± .15 | 62.52 ± 5.40 |

TABLE 1-continued

Hair Mass

| Compound | Dose | Vehicle | pH | Treated (mg) | Control (mg) | Percent Inhibition |
|---|---|---|---|---|---|---|
| Fenoprofen | 20% | D | 6.0 | 0.373 ± .10 | 1.276 ± .11 | 70.58 ± 7.04 |
| Ketoprofen | 20% | B | 4.5 | 0.895 ± .20 | 1.293 ± .26 | 29.70 ± 5.10 |
| Carprofen | 20% | C | 6.0 | 0.776 ± .11 | 1.274 ± .19 | 29.69 ± 11.06 |
| Indoleacetic acids | | | | | | |
| Indomethacin | 20% | A | 8.0 | 0.307 ± .08 | 1.844 ± .28 | 83.78 ± 3.66 |
| Sulindac | 20% | A | 9.0 | 0.517 ± .09 | 2.539 ± .27 | 79.90 ± 3.27 |
| Tolmetin | 20% | A | 8.5 | 1.459 ± .16 | 2.344 ± .24 | 37.85 ± 3.35 |
| Diclofenac | 20% | B | 8.0 | 0.648 ± .10 | 1.769 ± .19 | 63.40 ± 5.21 |
| Salicylates | | | | | | |
| Acetylsalicylic acid | 20% | B | 5.0 | 2.126 ± .33 | 3.194 ± .21 | 34.89 ± 7.91 |
| Diflunisal | 20% | D | 5.0 | 0.985 ± .10 | 1.779 ± .18 | 38.32 ± 10.73 |
| Anthranilic acids | | | | | | |
| Meclofenamic acid | 20% | A | 8.5 | 0.719 ± .14 | 2.144 ± .18 | 67.77 ± 4.79 |
| Mefenamic acid | 10% | A | 8.8 | 0.518 ± .13 | 1.520 ± .11 | 67.18 ± 6.03 |
| Enolic acids | | | | | | |
| Tenoxican | 15% | B | 8.0 | 0.326 ± .08 | 2.116 ± 0.24 | 85.38 ± 2.91 |
| Other | | | | | | |
| Nabumetone | 15% | E | 6.0 | 1.267 ± .23 | 1.684 ± .21 | 23.23 ± 10.41 |
| Quercetin | 5% | G | 6.0 | 1.100 ± .10 | 1.543 ± .10 | 27 ± 6 |
| | 10% | E | 5.5 | 0.419 ± .07 | 2.679 ± .22 | 83 ± 4 |
| Propyl gallate | 5% | B | 7.0 | 0.870 ± .15 | 2.553 ± .16 | 67 ± 5 |
| NDGA | 10% | B | 6.5 | 0.450 ± .11 | 2.391 ± .21 | 81 ± 4 |
| Caffeic acid | 5% | B | 6.0 | 1.740 ± .06 | 2.424 ± .17 | 26 ± 5 |
| | 15% | H | 4.0 | 0.797 ± .13 | 2.148 ± .22 | 62 ± 7 |

TABLE 2

Vehicles Used in Hair Mass Assays

| Vehicle A | 68% Purified water, 16% ethanol (200 proof), 5% propylene glycol, 5% dipropylene glycol, 4% benzyl alcohol, 2% propylene carbonate. |
|---|---|
| Vehicle B | 80% Ethanol (190 proof), 17.5% purified water, 2% propylene glycol dipelargonate, 0.5% propylene glycol. |
| Vehicle C | 30% Dipropylene glycol, 25% acetone, 15% ethanol (200 proof), 10% benzyl alcohol, 10% dimethyl sulfoxide (DMSO), 10% propylene glycol. |
| Vehicle D | 35% Dipropylene glycol, 30% ethanol (200 proof), 20% acetone, 10% propylene glycol, 5% benzyl alcohol. |
| Vehicle E | 35% Dipropylene glycol, 30% ethanol (200 proof), 25% acetone, 10% benzyl alcohol. |
| Vehicle F | 35% Dipropylene glycol, 35% ethanol (200 proof), 15% acetone, 10% DMSO, 5% benzyl alcohol. |
| Vehicle G | Acetone |
| Vehicle H | Moisturizing lotion containing common cosmetic ingredients which include emulsifiers, detergents, and preservatives. |

A preferred inhibitor, indomethacin, was tested for inhibition of hair growth in various formulations. The results are presented in Table 3.

TABLE 3

Hair Growth Inhibition by Indomethacin in Various Formulations

| Formulation | pH | Treated (mg) | Control (mg) | Percent Inhibition |
|---|---|---|---|---|
| 5% in Vehicle A | 7.5 | 1.248 ± .20 | 2.173 ± .14 | 43.41 ± 7.75 |
| 10% in Vehicle A | 7.5 | 1.084 ± .11 | 2.364 ± .22 | 53.32 ± 4.17 |
| 15% in Vehicle A | 7.5 | 0.768 ± .10 | 2.443 ± .15 | 68.77 ± 3.02 |
| 20% in Vehicle A | 8.0 | 0.307 ± .08 | 1.844 ± .28 | 83.78 ± 3.66 |
| 20% in Vehicle B | 7.0 | 0.261 ± .01 | 1.653 ± .15 | 83.37 ± 1.46 |
| 10% in Vehicle F | 5.5 | 0.679 ± .08 | 1.436 ± .20 | 49.89 ± 5.54 |
| 20% in Vehicle F | 5.5 | 0.324 ± .08 | 1.491 ± .14 | 78.43 ± 4.39 |

It will be appreciated by those skilled in the art that the invention can be performed within a wide range of equivalent parameters of composition and conditions without departing from the spirit or scope of the invention or of any embodiment thereof.

What is claimed is:

1. A method of treating unwanted mammalian hair growth, comprising,
   selecting an area of skin on a mammal from which reduced hair growth is desired; and
   applying to the area of skin a composition including nordihydroguaiaretic acid.

2. The method of claim 1, wherein the composition further comprises a non-toxic dermatologically acceptable vehicle.

3. The method of claim 1, wherein the mammal is a human.

4. The method of claim 1, wherein said concentration of said nordihydroguaiaretic acid in said composition is between 1% and 30%.

5. The method of claim 1, wherein the composition is applied to the skin in an amount of from 100 to 3000 micrograms of said nordihydroguaiaretic acid per square centimeter of skin.

6. The method of claim 1, wherein the composition is applied to an area of skin on the face of a human.

7. The method of claim 1, wherein the area of skin is on the arm of a human.

8. The method of claim 1, wherein the area of skin an on the leg of a human.

9. The method of claim 1, wherein the composition is applied to an area of skin on a human with hirsutism.

10. A method of treating unwanted mammalian hair growth, comprising, selecting an area of skin on a mammal from which reduced hair growth is desired; and applying to the area of skin a composition including a compound selected from the group consisting of quercetin, propyl gallate, and caffeic acid.

11. The method of claim 10, wherein the composition further comprises a non-toxic dermatologically acceptable vehicle.

12. The method of claim 10, wherein the mammal is a human.

13. The method of claim 10, wherein said concentration of said compound in said composition is between 1% and 30%.

14. The method of claim 10, wherein the composition is applied to the skin in an amount of from 100 to 3000 micrograms of said compound per square centimeter of skin.

15. The method of claim 10, wherein the composition is applied to an area of skin on the face of a human.

16. The method of claim 10, wherein the area of skin is on the arm of a human.

17. The method of claim 10, wherein the area of skin an on the leg of a human.

18. The method of claim 10, wherein the composition is applied to an area of skin on a human with hirsutism.

19. The method of claim 10, wherein the compound is quercetin.

20. The method of claim 10, wherein the compound is propyl gallate.

21. The method of claim 10, wherein the compound is caffeic acid.

* * * * *

UNITED STATES PATENT AND TRADEMARK OFFICE
CERTIFICATE OF CORRECTION

PATENT NO.   : 6,414,017 B2
DATED        : July 2, 2002
INVENTOR(S)  : Gurpreet S. Ahluwalia, Ph.D. and Douglas Shander It is certified that error appears in the above-identified patent and that said Letters Patent is hereby corrected as shown below:

Title page,
Item [75], Inventors, insert -- MD (US) --, after "Potomac"; replace "Gaithersburg" and insert -- Acton, MA (US) --, and delete "both of MD (US)".

Item [56], U.S. PATENT DOCUMENTS, replace "4,877,789" with -- 4,887,789 --.
FOREIGN PATENT DOCUMENTS, delete "GB 1458349 12/1976".

Column 4,
Line 62, replace "an" with -- is --.

Column 6,
Line 5, replace "an" with -- is --.

Signed and Sealed this

Twenty-fourth Day of December, 2002

JAMES E. ROGAN
*Director of the United States Patent and Trademark Office*